(12) United States Patent
Bhatt

(10) Patent No.: US 11,045,415 B2
(45) Date of Patent: Jun. 29, 2021

(54) HERB-BASED HAIR DYE AND METHOD FOR MANUFACTURING THE SAME

(71) Applicant: Sanjeev Bhatt, Haryana (IN)

(72) Inventor: Sanjeev Bhatt, Haryana (IN)

( * ) Notice: Subject to any disclaimer, the term of this patent is extended or adjusted under 35 U.S.C. 154(b) by 0 days.

(21) Appl. No.: 16/717,104

(22) Filed: Dec. 17, 2019

(65) Prior Publication Data

US 2020/0197291 A1 Jun. 25, 2020

Related U.S. Application Data

(60) Provisional application No. 62/781,726, filed on Dec. 19, 2018.

(51) Int. Cl.
| | | |
|---|---|---|
| *A61Q 5/10* | (2006.01) | |
| *A61K 8/97* | (2017.01) | |
| *A61L 2/00* | (2006.01) | |

(52) U.S. Cl.
CPC .............. *A61K 8/97* (2013.01); *A61L 2/0023* (2013.01); *A61Q 5/10* (2013.01); *A61K 2236/15* (2013.01); *A61K 2236/17* (2013.01); *A61K 2800/5922* (2013.01); *A61K 2800/70* (2013.01); *A61L 2202/21* (2013.01)

(58) Field of Classification Search
CPC .. A61Q 5/10; A61K 2236/31; A61K 2236/51; A61K 2236/15; A61K 2236/11; A61K 2236/17; A61K 8/97; A61K 2800/5922; A61K 2800/70; A61L 2/0023; A61L 2202/21
USPC ........................................................... 8/405
See application file for complete search history.

(56) References Cited

U.S. PATENT DOCUMENTS

2014/0048093 A1* 2/2014 Bernet ..................... A61Q 5/10
132/208

\* cited by examiner

*Primary Examiner* — Eisa B Elhilo
(74) *Attorney, Agent, or Firm* — Browdy and Neimark, P.L.L.C.

(57) ABSTRACT

A herb-based hair dye formulation includes one or more ingredients selected from coloring agent, enhancing agent, toning agent and auxiliary agent of herb origin. Also disclosed is a method for producing a herb-based product, and particularly a method for manufacturing the herb-based hair dye formulation.

22 Claims, No Drawings

HERB-BASED HAIR DYE AND METHOD FOR MANUFACTURING THE SAME

CROSS-REFERENCE TO RELATED APPLICATIONS

This application is a Non-Provisional of U.S. application Ser. No. 62/781,726 filed Dec. 18, 2018. The above application is hereby expressly incorporated by reference, in its entirety, into the present application.

FIELD OF THE INVENTION

This invention relates generally to hair dye, and particularly to herb-based hair dye having herbal ingredients and method for manufacturing the same.

BACKGROUND OF THE INVENTION

There is an increasing demand in the market for organic products, including organic foods, clothing and personal care products. Little to none synthetic chemical is used during production of organic products, or no synthetic chemical additive exists in the final product. It is considered that organic products are more natural, healthy and safe to consumers, while being sustainable, conservational and eco-friendly to the Mother Earth.

Today, hair dyes are widely used, either to cover up grey hairs, or simply by those who desire to change their natural hair color. A number of hair dyes contain chemicals that are known irritants to irritate the skin, eyes and respiratory system. These chemicals might be quite harsh and can harden or thin the hair. Furthermore, the chemicals-based hair dyes are not suitable for people who are prone to allergies. Accordingly, it is of great need to provide organic hair dyes.

SUMMARY OF THE INVENTION

An object of the invention is to provide an organic hair dye formulation comprised of all natural ingredients, specifically herbal active ingredients obtained by processing plant parts such as leaves, flowers, fruits, seeds, roots, etc. The herb-based hair dye of the invention does not contain harmful synthetic chemicals such as ammonia, formaldehyde, peroxides, dioxanes, diaminobenzenes, diphenols and preservatives which typically exist in conventional synthetic hair dyes and may cause allergy, skin irritation, hair damage and other health concerns. The herb-based hair dye of the invention not only gives a natural color tone to hair, but also enriches hair and skin, promotes hair growth and provides hair treatment properties and other health care effects to the user.

In a first aspect, the present invention provides a herb-based hair dye formulation comprising:
(1) one or more coloring agents of herb origin;
(2) one or more enhancing agents of herb origin to enhance coloring effects of the coloring agents;
(3) a toning agent of herb origin to condition a color tone of the hair; and
(4) optionally one or more auxiliary agents of herb origin.

In the herb-based hair dye formulation of the present invention, the respective agents are herbal active ingredients obtained by processing plant parts.

In a preferred herb-based hair dye formulation, the coloring agent is selected from a group consisting of Henna, Indigo, Manjistha, Turmeric, *Hibiscus*, Indigo extract, and any combination thereof; the enhancing agent is selected from a group consisting of Amla, Bhrami, Bhringraj, Methi, and any combination thereof; the toning agent is selected from *Cassia*; and the auxiliary agnet is selected from a group consisting of Reetha, Shikakai, and any combination thereof.

In preferred embodiments of the herb-based hair dye formulation of the invention, Heena may account for 2 to 16 wt %, 17 to 34 wt %, 35 to 60 wt %, or 80 to 98% of the hair dye formulation; and/or Indigo may account for 0.5 to 30 wt %, or 35 to 86 wt % of the hair dye formulation; and/or Manjistha may account for 0.5 to 3 wt %, 4 to 7 wt %, or 10 to 60 wt % of the hair dye formulation; and/or Turmeric may account for 30 to 45 wt % of the hair dye formulation; and/or *Hibiscus* may account for 0.5 to 7 wt %, or 28 to 32 wt % of the hair dye formulation; and/or Indigo extract may account for 1.5 to 4 wt % of the hair dye formulation; and/or Amla may account for 0.5 to 12 wt %, 23 to 27 wt %, 28 to 35 wt %, or 70 to 75 wt % of the hair dye formulation; and/or Bhrami may account for 0.5 to 2 wt %, or 23 to 27 wt % of the hair dye formulation; and/or Bhringraj may account for 0.5 to 2 wt %, or 23 to 27 wt % of the hair dye formulation; and/or Methi may account for 0.5 to 10 wt % of the hair dye formulation; and/or *Cassia* may account for 0.5 to 45 wt %, or 55 to 95.5 wt % of the hair dye formulation; and/or Reetha may account for 0.5 to 10 wt %, or 18 to 35 wt % of the hair dye formulation; and/or Shikakai may account for 0.5 to 10 wt %, or 18 to 35 wt % of the hair dye formulation.

Most preferred herb-based hair dye formulations of the present invention are listed in Table 1 of the description. In the herb-based hair dye formulations, the above agents (1) to (4) add up to 100 wt %.

In further embodiments, the herb-based hair dye formulation further comprises one or more further agents selected from a wetting agent, a hair conditioner, and an agent that imparts treatment effects to hair. The treatment effects include cleaning the hair, softening a texture of the hair, and making the hair strong, silky and shiny In a second aspect, the present invention provides a method for producing herb-based product, comprising the following steps of:
(1) providing fresh plant parts of desirable herbs;
(2) freeze drying of the fresh plant parts under a condition that allows for freezing of water and removal of the water from the plant parts;
(3) steam sterilization of the freeze-dried plant parts for a given duration of time to sterilize the plant parts so as to obtain the herbal ingredients; and
(4) mixing of different herbal ingredients in a desirable ratio.

Preferably, the step of freezing drying is carried out under the combined effect of a temperature ranging from −70° C. to −40° C. and vacuum pressure to remove the water by sublimation. Preferably, the step of steam sterilization is carried out at a temperature ranging from 110° C. to 140° C.

In preferred embodiments, the above method further comprising a step of grinding the freeze-dried plant parts into powder, and an optional step of sieving the plant part powders in order to remove any foreign body or impurities.

In preferred embodiments, the above method further comprising a step of storing the freeze-dried plant parts in vacuum packing before the steps of grinding, sterilization or mixing.

In preferred embodiments, the above method further comprising a step of packing the mixed herbal ingredients.

Particularly, in the method of the second aspect of the present invention, the product produced by the method is a herb-based hair dye formulation, and the herbs provided in step (1) are selected to formulate the hair dye formulation, and the herbal ingredients in the step (4) are mixed in a ratio adapted for formulating the hair dye formulation.

In preferred embodiments, the above method further comprising the step of packing the mixed hair dye.

In other words, the present invention provides a method for manufacturing a herb-based hair dye formulation, the method comprising the following steps of:

(1) providing fresh plant parts of desirable herbs which are being used to formulate a hair dye formulation;
(2) freeze drying of the fresh plant parts under a condition that allows for freezing of water and removal of the water from the plant parts;
(3) steam sterilization of the freeze-dried plant parts for a given duration of time to sterilize the plant parts so as to obtain the herbal ingredients;
(4) mixing of different herbal ingredients in a ratio adapted for the hair dye formulation; and optionally
(5) packing of the mixed hair dye.

Obviously, the method for producing herb-based hair dye formulation is useful for manufacturing the herb-based hair dye formulation provided in the first aspect of the present invention.

More particularly and advantageously, in the method of the second aspect of the present invention, the freeze drying is carried out to remain and save 100% active and passive agents as present in herbs when they are live on plant in the freeze-dried plant parts.

Preferably, the above method further comprising the steps of storing the freeze-dried herb parts in vacuum pack and microfine-grinding the herb parts in powder form before the mixing step.

Preferably, in the above method, the mixing step comprising mixing the herbal powders in required ratios for the formulations of different colors.

Preferably, the above method further comprising the steps of subjecting the premixed herbal powders to steam sterilization and packing the powders in desired quantity and required packs.

In other words, the present invention provides a most preferred method for manufacturing a herb-based hair dye formulation, the method comprising the following steps in the following sequence:

(1) providing fresh plant parts of desirable herbs which are being used to formulate a hair dye formulation;
(2) freeze drying of the fresh plant parts to remove water from the plant parts by method of sublimation; 100% active and passive agents as present in herbs when it is live on plant are protected and saved during the step of freeze drying;
(3) storing the freeze-dried herb parts in vacuum pack;
(4) microfine grinding of freeze-dried herbs parts to convert into a smooth powder;
(5) mixing of different herbal powders in required ratios as per formulation in order to make different colors;
(6) steam sterilization of premixed powder; and
(7) packing of powders in desired quantity and required packs.

DETAILED DESCRIPTION OF EMBODIMENTS

The present invention together with the preferred embodiments for carrying out the invention will be described in detail in the following.

The herb-based hair dye formulation of the invention in a first aspect comprises:

(1) one or more coloring agents selected from a group consisting of Henna, Indigo, Manjistha, Turmeric, *Hibiscus*, Indigo extract, and any combination thereof;
(2) one or more enhancing agents selected from a group consisting of Amla, Bhrami, Bhringraj, Methi, and any combination thereof;
(3) a toning agent selected from *Cassia*; and
(4) optionally one or more auxiliary agents selected from a group consisting of Reetha, Shikakai, and any combination thereof.

In the herb-based hair dye formulations, the coloring agents give different color shades to hair. In particular, Henna gives orangish coloring tone; Indigo gives blue coloring tone; Manjistha gives red coloring tone; Turmeric gives yellow coloring tone; *Hibiscus* gives pink coloring tone; and Indigo extract gives deep purple coloring tone.

The enhancing agents enhance coloring effects imparted by the main coloring ingredients. The enhancing agents can help in darkening the hair color and enhancing the color intensity.

The toning agent can dilute the excess color tone imparted by the coloring agents and enhancing agents in order to give desired color tone.

The auxiliary agents mainly provide additional hair treatment properties and caring effects to hair, including cleaning the hair, softening a texture of the hair, as well as making hair strong, soft, silky and shiny.

More specifically, herbal origin, weight percentage and effects of each ingredient in the herb-based hair dye formulation are as follows.

As used herein, term "Henna" refers to material obtained from leaves of *Lawsonia inermis*. Henna may account for 2-98 wt % of the hair dye formulation if present. Aside from hair coloring, Henna also acts as an astringent agent, boosts hair growth, cools scalp and skin, treats dandruff, and makes hair shine.

Depending on the type of formulation, Heena may account for 2 to 16 wt %, 17 to 34 wt %, 35 to 60 wt %, or 80 to 98% of the hair dye formulation.

As used herein, term "Indigo" refers to material obtained from leaves of *Indigofera tinctoria*. Indigo may account for 0.5-86 wt % of the hair dye formulation if present. Aside from hair coloring, Indigo also provides masking, toning and antiseptic effects.

When Indigo accounts for 0.5 to 30 wt % of the formulation, the hair dye formulation may be applied for obtaining a lighter hair color, such as blonde or light brown; when Manjistha accounts for 35 to 86 wt % of the formulation, the hair dye formulation may be applied for obtaining a darker hair color tone, such as red, brown, violet or black.

As used herein, term "Manjistha" refers to material obtained from roots of *Rubia cordifolia*. Manjistha may account for 0.5-65 wt % of the hair dye formulation if present. Aside from hair coloring, Manjistha is very effective in preventing hair loss, dandruff and type of skin problem, while also helps in darkening color.

When Manjistha accounts for 0.5 to 3 wt % of the formulation, the color of the hair dye formulation is not substantially affected by Manjistha; when Manjistha accounts for 4 to 7 wt % of the formulation, the color of the hair dye formulation may comprise a reddish component; when Manjistha accounts for 10 to 60 wt % of the formulation, the hair dye formulation may be applied for obtaining a red hair color tone.

As used herein, term "Turmeric" refers to material obtained from roots of *Curcuma longa*. Turmeric may account for 30-45 wt % of the hair dye formulation if present. Aside from hair coloring, compound curcumin in Turmeric has potent antioxidant and anti-inflammatory properties that could help resolve underlying conditions which cause hair loss.

As used herein, term "*Hibiscus*" refers to material obtained from flowers of *Hibiscus rosa sinensis*. *Hibiscus* may account for 0.5-32 wt % of the hair dye formulation if present. Aside from hair coloring, *Hibiscus* has great cooling properties, prevents dandruff and adds shine to hair.

When *Hibiscus* accounts for 0.5 to 7 wt % of the formulation, the color of the hair dye formulation may comprise a reddish component; when *Hibiscus* accounts for 28 to 32 wt % of the formulation, the hair dye formulation may be applied for obtaining a blonde hair color tone.

As used herein, term "Indigo extract" refers to material obtained from Extract of *Indigofera tinctoria*. Indigo extract may account for 1.5-4 wt % of the hair dye formulation if present. Aside from hair coloring, Indigo extract also provides masking, toning and antiseptic effects, similar as Indigo.

As used herein, term "Amla" refers to material obtained from fruits of *Phyllanthus emblica*. Amla may account for 0.5-75 wt % of the hair dye formulation if present. Amla helps in darkening hair color imparted by other herbs. Amla is rich in anti-oxidant Vitamin C, tannins, prevents naturally greying of hair, promotes hair growth and improve its retention.

When Amla accounts for 0.5 to 12 wt % of the formulation, the color of the hair dye formulation is not substantially affected by Amla; when Amla accounts for 23 to 27 wt % of the formulation, the hair dye formulation may be applied for obtaining a light brown hair color tone; when Amla accounts for 28 to 35 wt % of the formulation, the hair dye formulation may be applied for conditioning the hair and enhancing the hair color; when Amla accounts for more than 70 wt % of the formulation, the hair dye formulation may be applied for obtaining a blonde hair color tone.

As used herein, term "Bhrami" refers to material obtained from leaves of *Bacopa monnieri*. Bhrami may account for 0.5-2 wt % of the hair dye formulation if present. In certain embodiments, Bhrami may account for 23 to 27 wt % of the hair dye formulation. Bhrami enhances the color intensity imparted by other herbs. Bhrami promotes health of hair and skin, reduces hair loss and dandruff, and may also strengthen memory of user.

As used herein, term "Bhringraj" refers to material obtained from leaves of *Eclipta alba*. Bhringraj may account for 0.5-2 wt % of the hair dye formulation if present. In certain embodiments, Bhringraj may account for 23 to 27 wt % of the hair dye formulation. Bhringraj helps in darkening hair color imparted by other herbs. Bhringraj is also antioxidant, anti-bacterial, rich in alkaloids and proteins, which helps in hair retention through revitalizing hair follicles by stimulating blood circulation.

As used herein, term "Methi" refers to material obtained from seeds of *Trigonella foenum-graecum*. Methi may account for 0.5-10 wt % of the hair dye formulation if present. Methi enhances the color intensity imparted by other herbs and helps in fixing color. Methi also exhibits hair treatment properties, such as helping hair growth, controlling dandruff, premature hair loss and seasonal irritations of scalp.

As used herein, term "*Cassia*" refers to material obtained from leaves of *Cassia auriculata* or *Cassia obovata*. *Cassia* may account for 0.5-95 wt % of the hair dye formulation if present. *Cassia* dilutes the excess color intensity imparted by other herbs in order to achieve desired color tone. It also extends hair treatment properties, including cooling scalp and skin, treating dandruff, making hair shine as well as hair conditioning effects. In some cases, *Cassia* is also called as "Colorless henna" or "Seena", as it extends hair treatment properties like henna but do not impart any color to hair.

When *Cassia* accounts for 55 to 95 wt % of the formulation, the hair dye formulation may be applied for obtaining a blonde hair color tone; when *Cassia* accounts for 0.5 to 45 wt % of the formulation, the hair dye formulation may be applied for obtaining a brown hair color tone.

As used herein, term "Reetha" refers to material obtained from fruits of *Sapindus mukorossi*. Reetha may account for 0.5-1.0 wt % of the hair dye formulation if present. Reetha can clean hair and is considered good for the health of hair. Reetha may also enhance the color intensity imparted by other herbs.

In alternate embodiment, Reetha may account for 18 to 35 wt % of the formulation of the present invention, for conditioning the hair and enhancing the hair color.

As used herein, term "Shikakai" refers to material obtained from fruits of *Acacia concinna*. Shikakai may account for 0.5-1.0 wt % of the hair dye formulation if present. Shikakai has hair conditioning effects. It gently cleans the hair without stripping it of natural oils. Shikakai also controls dandruff, promotes hair growth and strengthens hair roots. Shikakai may also enhance the color intensity imparted by other herbs.

In alternate embodiment, Shikakai may account for 18 to 35 wt % of the formulation of the present invention, for conditioning the hair and enhancing the hair color.

In the herb-based hair dye formulations of the invention, the above agents (1) to (4) add up to 100% by weight.

It is understandable that the color of the hair dye formulation is determined by one or more of the ingredients. In other words, the color may substantially depend on the coloring agents. The color may also depend on the combination of a plurality of agents as a whole. It is also understandable that the color of the hair dye formulation can be different from the resulting color of hair dyed with the formulation. The factors may include the original hair color, amount of hair dye used, duration of hair dye applied on hair and the like.

Advantageously, the herb-based hair dye of the invention is presented in powdered form as a mixture of blend of the ingredients. Accordingly, the invention relates to a method for the extraction of herbs.

Provided in a second aspect of the invention is a method for producing herb-based product, comprising the following steps of:
1. Providing fresh plant parts of desirable herbs;
2. Freeze drying of the fresh plant parts under a condition that allows for freezing of water and removal of the water from the plant parts;
3. Steam sterilization of the freeze-dried plant parts for a given duration of time to sterilize the plant parts so as to obtain the herbal ingredients; and
4. Mixing of different herbal ingredients in a desirable ratio.

Particularly, the step 1 of providing fresh plant parts may include organic cultivation of herbs and ploughing of the fresh plant parts of herbs.

Particularly, the step 2 of freezing drying is carried out under the combined effect of a temperature ranging from −70° C. to −40° C. and vacuum pressure to remove the water by sublimation.

Particularly, the step 3 of steam sterilization is carried out at a temperature ranging from 110° C. to 140° C.

Preferably, the method of the invention comprises a step of grinding the freeze-dried plant parts into powder, for example, using very special pulverisers and micro fine grinding machines; and optionally comprises a step of sieving the plant part powders in order to remove any foreign body or impurities, for example, sieving through 80 to 125 mesh.

The method further comprises a step of storing the freeze-dried plant parts in vacuum packing before further processing such as grinding, sterilization and mixing.

The method may optionally comprise a step of packing of the mixed herbal ingredients after the mixing step 4.

It should be understood that the method of the invention is not limited to be implemented according to the above-listed order. For example, steam sterilization can be performed prior to the mixing of different herbal ingredient or after the mixing; sieving can be carried out following the grinding, or immediately before the packing.

The method can find a wide range of applications. In one embodiment of the invention, the method is useful for manufacturing the herb-based hair dye discussed herein above, comprising the steps of:
1. Providing fresh plant parts of desirable herbs which are being used to formulate a hair dye formulation;
2. Freeze drying of the fresh plant parts under a condition that allows for freezing of water and removal of the from the plant parts;
3. Steam sterilization of the freeze-dried plant parts for a given duration of time to sterilize the plant parts so as to obtain the herbal ingredients;
4. Mixing of different herbal ingredients in a ratio adapted for the hair dye formulation;
   and optionally
5. Packing of the mixed hair dye.

In another embodiment of the invention, the method is useful to manufacturing natural Chinese or Ayurvedic medicines which require extraction of herbs which are suitable for medicinal purpose. The freeze-drying method of the invention will make the herbs very strong with all active ingredients alive and highly concentrated in the powder ingredients, which can be further processed for medicinal uses.

The most significant achievement of the present invention is 100% active ingredients present in the live plant parts are secured and protected in the extracted herbs, particularly herb-based hair dye of the invention. A scientific process of sublimation is used in the method of the invention for the removal of water without boiling the herbs, hence secures and protects 100% active ingredients, most of which will otherwise die as soon as they are removed from plants. As a result, efficacy of each herb is increased manifold as it becomes highly concentrated with all active ingredients without losing any active ingredients, in contrast to the conventional process of drying herbs where most of the active ingredients die.

Sublimation is the transition of a substance directly from solid phase to gas phase. Sublimation occurs at temperatures and pressures below a substance's triple point in its phase diagram. Triple point of a substance is the temperature and pressure at which the three phases (gas, liquid, and solid) of that substance coexist in thermodynamic equilibrium, which corresponds to the lowest pressure at which the substance can exist as a liquid. For example, water has a triple point at a temperature of 0.1° C. and a pressure of 0.611 kPa. That is, at a temperature below 0.1° C. and a pressure below 0.611 kPa, solid water—ice will convert directly into water vapor without boiling. For this purpose, freezing drying method is adopted by using freeze drying machines.

During freeze drying procedure according to the method of the invention, plant parts such as leaves are freezed first at a temperature below −40° C. and above −70° C., much below the triple point causing freezing of water in herbs to solid ice. Then the freezed plant parts are placed under deep vacuum, where a very low pressure is created for sublimation process to take place. By using an optimum combination of vacuum pressure and temperature, all solid ice can be removed and converted directly into gas (water vapor) by sublimation, hence keeping the herbs in original state without any changes. After freeze drying, the remaining would be in purest form of plant parts with 100% active ingredients alive and with no change in size, shape, odor, color, etc., keeping the active ingredients intact as if it was live in plant.

As soon as the parts of plants, for example leaves, fruits, seeds or the like are cut, active agents present in herbs start decaying and dying. For example, leaves are dark green when these are live on plant due presence of one active agent called chlorophyll. Once leaves are removed from plant, chlorophyll content start decaying and dying. In a few hours, leaves become brown instead of dark green and soon in few days turn into yellowish.

To protect and preserve all active ingredients in plant parts, all water must be removed as soon as the plant parts are cut from plant. Fresh leaves may contain water by more than 95 wt %; and water causes decay of almost 98% of active ingredients.

However, in conventional methods, the cut plant parts are either sun-dried or air-dried just naturally with time in storage before converting into powder, hence most of the active ingredients present in the plant dies. Final products are made using these herb powders which may contain less than approximately 2% of original active ingredients which were present when herbs were alive on plant.

Another conventional method known in the art to make herb's efficacy a little bit stronger is to make extract out of herbs. Extracts are concentrated forms of active agents present in the herbs. The conventional method of extraction is first to soak plant parts such as leaves in either water or in alcohol solvent for a certain period of time, for example 48 hours, subsequently water is strained and separated from leaves by filtration. This water contains active agents which are passed from leaves to water. Then water is evaporated by boiling at 100° C. and what remains are powder of active ingredients, which are then used to make herb's efficacy stronger.

But it has been found that while in storage approximately 98% active ingredients die and only approximately 2% active ingredients pass on to water or alcohol during extraction process. Moreover, when water is boiled for evaporation, active agents start dying further after temperature of 70° C., and it is estimated that almost 99.5% of active agents die at 100° C. Hence 99.5% of the remaining 2% active ingredients also die after boiling, it means only approximately 0.01% of the original active ingredients remain in the extract.

Prior to the present invention, due to above mentioned reasons herbs are very weak and slow in efficacy and in extending desired results to body in comparison to synthetic chemicals.

Unlike the conventional methods, according to the method of the present invention 100% of active agents would remain intact, protected and saved, hence herbs become many times stronger in efficacy. Accordingly, benefits of herbs to hair and body also increase manifold and time to achieve results would also decrease manifold With this invention herbs may become either stronger or at least equal to synthetic chemicals in terms of efficacy and extending desired results to body. Since herbs are safe and do not have adverse side effects like synthetic chemicals, this invention may provide significant benefits to society by making it safe and healthy not only in just hair dyes but also in medicine world.

Freeze-dried plant parts may be packed in vacuum packing for storage before further processing. In this way, no moisture can contact the plant parts and the freeze-dried plant parts maintain the original freshness as in field with 100% active ingredients remain intact as if in live plants.

Micro fine grinding of herbs parts can be carried out in order to get very fine particles and smooth herb powder, so that micro particles can enter the hair deep inside in order to give intense color tone and long-retention of color on hair, as well as extend very strong hair treatment properties and also shorten the application time on hair.

The grinded herb powder ingredients may be mixed in a particular ratio adapted for each hair dye formulation, and sieved through 80 to 125 mesh in order to remove any impurities.

Steam sterilization of the fine herbal powder mix is conducted in order to kill any contamination or microbes which might have survived the low temperature during freeze drying process. The steam sterilization process shall be carried out under an optimum combination of temperature, pressure and vacuum where the powders of freeze-dried plant parts are exposed to steam for a very short duration. Typically, steam sterilization is performed at a temperature of 110° C. to 140° C. for a short duration of time. The higher the steam temperature, the shorter the sterilization duration. The steam sterilization process makes the herbal ingredients absolutely free of any contamination and microbes, and it also converts the passive agents in herbs into active state hence further enhancing the efficacy of herbs to its maximum possible and reaching an epitome in its properties. After steam sterilization, herbs will become even more strong and effective and will also reduce time in giving the desire results.

It is understood from the above manufacturing method that the herb-based hair dye formulations of the invention are in solid form, preferably as powders, in contrast to the conventional synthetic hair dyes which typically exists in liquid, paste or gel forms.

In a particularly preferred embodiment, the method for manufacturing the herb-based hair dye according to the present invention, comprises the following steps in the following sequence:
1. Providing fresh plant parts of desirable herbs which are being used to formulate a hair dye formulation;
2. Freeze drying of the fresh plant parts to remove water from the plant parts by method of sublimation; 100% active and passive agents as present in herbs when it is live on plant are protected and saved during the step of freeze drying;
3. Storing the freeze-dried herb parts in vacuum pack;
4. Microfine grinding of freeze-dried herbs parts to convert into a smooth powder;
5. Mixing of different herbal powders in required ratios as per formulation in order to make different colors;
6. Steam sterilization of premixed powder; and
7. Packing of powders in desired quantity and required packs.

Preferred hair dye formulations of the invention are listed in the following Table 1.

TABLE 1

Composition of the herb-based hair dye formulations.

| Formulation | color tone | Henna | Indigo | Manjistha | Turmeric | *Hibiscus* | Indigo extract | Amla |
|---|---|---|---|---|---|---|---|---|
| # 1 | black | 14.2-16.5 | 78.75-81.5 | 1.8-2.5 | | | | 0.95-1.5 |
| # 2 | brown | 31-34.5 | 63-65.5 | 0.45-0.75 | | 0.45-0.75 | | 0.45-0.75 |
| # 3 | brown | 44-47.5 | 47.75-52 | 0.95-1.25 | | 0.95-1.25 | | 0.45-0.75 |
| # 4 | brown | 37-42 | 47.5-52.5 | 4.7-6.25 | | 2.3-3.25 | | 0.45-0.75 |
| # 5 | red | 38-43 | | | 55-60 | 0.45-0.625 | | 0.45-0.625 |
| # 6 | red | 44.5-50 | 34.5-40 | 9.5-12.25 | | 4.7-6.5 | | 0.45-0.625 |
| # 7 | red brown | 55-60 | 38-43 | | | 0.45-0.625 | | 0.45-0.625 |
| # 8 | blonde | 28.5-32 | 26.5-30 | 0.45-0.625 | | 0.45-0.625 | | 0.45-0.625 |
| # 9 | blonde | 28.5-32 | | | | 0.95-1.25 | | 1.9-2.25 |
| # 10 | red | 84-87 | 9-12 | | | 0.95-1.25 | | 1.9-2.25 |
| # 11 | brown | 28-32 | 35-38 | 0.45-0.625 | | 0.45-0.625 | | 0.95-1.25 |
| # 12 | blonde brown | | 0.45-0.625 | | | | | 23-27 |
| # 13 | blonde | | 23.5-28.5 | | | | | 70-75 |
| # 14 | blonde brown | | 23.5-27 | | | | | 23.5-27 |
| # 15 | blonde | 23.5-27 | 23.5-27 | | | | 28.5-32 | 9.5-11.5 |
| # 16 | violet | | 76-82 | 4-6.25 | | 4-6.25 | | |
| # 17 | blonde | | 7-10.25 | | | | | 0.45-0.625 |
| # 18 | blonde | 7-10.25 | | | | | | 0.45-0.625 |
| # 19 | red | 18-22 | 8-10 | | | | | 0.45-0.625 |
| # 20 | blonde | 4-6.25 | 6.5-8.5 | | | | | 0.45-0.625 |
| # 21 | red | 6.5-8.5 | 4-6.25 | | | | | 0.45-0.625 |
| # 22 | blonde | 2.5-3.5 | | | | | | 0.45-0.625 |
| # 23 | blonde | 1.75-2.25 | | 0.9-1.25 | | 0.45-0.625 | | 0.45-0.625 |
| # 24 | black | 8.8-11 | 82-85 | 1.75-2.25 | | | 1.75-2.25 | 0.9-1.25 |
| # 25 | brown | 17-20 | 71-75 | 5-6.5 | | | 3-5 | |
| # 26 | brown | 35-39 | 52-57 | 5-6.5 | | | 2-3 | |
| # 27 | no color | | | | | | | 32-35 |
| # 28 | brown | 97.5-98.2 | | | | | | 0.45-0.625 |
| # 29 | brown | 82-87 | 9-12 | | | | | |
| # 30 | brown | 28.5-32 | 26.5-30 | | | | | |
| # 31 | brown | 35-39 | 58-62 | | | | | |
| # 32 | brown | 13-16 | 83-86 | | | | | |

TABLE 1-continued

Composition of the herb-based hair dye formulations.

| # 33 | no color | | | | | | 28.5-33 | |
| # 34 | brown | 38-43 | 57-62 | | | | | |
| # 35 | blonde | | | | 35.5-37.5 | | | 0.45-0.625 |

| Formulation | color tone | Bhrami | Bhringraj | Methi | Cassia | Reetha | Shikakai |
|---|---|---|---|---|---|---|---|
| # 1 | black | | 0.45-0.75 | | | | |
| # 2 | brown | | 0.45-0.75 | 0.45-0.75 | | | |
| # 3 | brown | | 0.45-0.75 | 0.45-0.75 | | | |
| # 4 | brown | | 0.45-0.75 | 2.3-3.25 | | | |
| # 5 | red | | 0.45-0.625 | 0.45-0.625 | | | |
| # 6 | red | | 0.45-0.625 | | | | |
| # 7 | red brown | | 0.45-0.625 | 0.45-0.625 | | | |
| # 8 | blonde | | 0.45-0.625 | | 38-42 | | |
| # 9 | blonde | | 0.95-1.25 | 0.95-1.25 | 63-66.5 | | |
| # 10 | red | | 0.95-1.25 | | | | |
| # 11 | brown | | 0.45-0.625 | | 28.5-32 | | |
| # 12 | blonde brown | 0.45-0.625 | 0.45-0.625 | | 71.25-75.5 | | |
| # 13 | blonde | 0.45-0.625 | 0.45-0.625 | | 0.45-0.625 | | |
| # 14 | blonde brown | 23.5-27 | 23.5-27 | | | | |
| # 15 | blonde | | | 9.5-11.5 | | | |
| # 16 | violet | | | 9.5-12.5 | | | |
| # 17 | blonde | 0.45-0.625 | 0.45-0.625 | | 88-92 | | |
| # 18 | blonde | 0.45-0.625 | 0.45-0.625 | | 88-92 | | |
| # 19 | red | 0.45-0.625 | 0.45-0.625 | | 68-72 | | |
| # 20 | blonde | 0.45-0.625 | 0.45-0.625 | | 84-88 | | |
| # 21 | red | 0.45-0.625 | 0.45-0.625 | | 84-88 | | |
| # 22 | blonde | 0.45-0.625 | 0.45-0.625 | 0.45-0.625 | 94-95.5 | | |
| # 23 | blonde | 0.45-0.625 | 0.45-0.625 | | 94-95.5 | | |
| # 24 | black | 0.9-1.25 | 0.9-1.25 | | | | |
| # 25 | brown | | | | | | |
| # 26 | brown | | | | | | |
| # 27 | no color | | | | | 31-35 | 31-35 |
| # 28 | brown | | 0.45-0.625 | | | 0.45-0.625 | 0.45-0.625 |
| # 29 | brown | | | | 4-6.25 | | |
| # 30 | brown | | | | 39.5-44 | | |
| # 31 | brown | | | | 2.8-4 | | |
| # 32 | brown | | | | 0.9-1.25 | | |
| # 33 | no color | | | | 28.5-33 | 19-22 | 19-22 |
| # 34 | brown | | | | | | |
| # 35 | blonde | 0.45-0.625 | 0.45-0.625 | | 57.5-62 | 0.45-0.625 | 0.45-0.625 |

All numbers are wt % in the above table.

It should be understood that the present invention is not limited to above specific formulations.

When using the hair dyes of the present invention, the powdered formulation packed in paper bag is mixed with hot water in sufficient quantity in order to make a smooth paste having a consistency like tomato ketchup or yogurt, which is quite convenient in applying to hair starting from roots and covering the hair properly. This paste is applied on hair for a certain period of time for achieving the desired coloring effect.

In addition, although the hair dyes of the present invention are in powdered form, the hair dye can also be manufactured into shampoo by treating the powder with water or other solvent so as to dissolve the active ingredients from the herbal ingredients. Additives can be also be added for making a proper shampoo.

In summary, the invention provides organic hair dye formulation comprised of 100% natural and organic herbal ingredients. The herb-based hair dyes are capable of achieving desirable coloring effects on hair and providing other hair treatment and health care effects without any adverse effects resulted from the harmful chemicals in synthetic hair dyes.

Above described are preferred embodiments of the herb-based hair dye of the present invention. It is understood that the present invention is not limited to the above embodiments and any appropriate modifications can be adopted within the scope of the present invention as long as they can achieve the effects of the present invention.

What is claimed is:

1. A herb-based hair dye formulation comprising:
   (1) one or more coloring agents of herb origin;
   (2) one or more enhancing agents of herb origin to enhance coloring effects of the coloring agents;
   (3) a toning agent of herb origin to condition a color tone of the hair; and
   (4) optionally one or more auxiliary agents of herb origin
   wherein the coloring agent is selected from a group consisting of Henna, Indigo, Manjistha, Turmeric, *Hibiscus*, Indigo extract, and any combination thereof
   wherein the coloring agent includes one or more of the following:
   Heena accounts for 2 to 16 wt %, 17 to 34 wt %, 35 to 60 wt %, or 80 to 98% of the hair dye formulation;
   Indigo accounts for 0.5 to 30 wt %, or 35 to 86 wt % of the hair dye formulation;
   Manjistha accounts for 0.5 to 3 wt %, 4 to 7 wt %, or 10 to 60 wt % of the hair dye formulation;
   Turmeric accounts for 30 to 45 wt % of the hair dye formulation;
   *Hibiscus* accounts for 0.5 to 7 wt %, or 28 to 32 wt % of the hair dye formulation; and
   Indigo extract accounts for 1.5 to 4 wt % of the hair dye formulation.

2. The herb-based hair dye formulation according to claim 1, wherein the enhancing agent is selected from a group consisting of Amla, Bhrami, Bhringraj, Methi, and any combination thereof.

3. The herb-based hair dye formulation according to claim 2, wherein the enhancing agent includes one or more of the following:
Amla accounts for 0.5 to 12 wt %, 23 to 27 wt %, 28 to 35 wt %, or 70 to 75 wt % of the hair dye formulation;
Bhrami accounts for 0.5 to 2 wt %, or 23 to 27 wt % of the hair dye formulation;
Bhringraj accounts for 0.5 to 2 wt %, or 23 to 27 wt % of the hair dye formulation; and
Methi accounts for 0.5 to 10 wt % of the hair dye formulation.

4. The herb-based hair dye formulation according to claim 1, wherein the toning agent is selected from *Cassia*.

5. The herb-based hair dye formulation according to claim 4, wherein *Cassia* accounts for 0.5 to 45 wt %, or 55 to 95.5 wt % of the hair dye formulation.

6. The herb-based hair dye formulation according to claim 1, wherein the auxiliary agent is selected from a group consisting of Reetha, Shikakai, and any combination thereof.

7. The herb-based hair dye formulation according to claim 6, wherein the auxiliary agent includes one or more of the following:
Reetha accounts for 0.5 to 10 wt %, or 18 to 35 wt % of the hair dye formulation; and
Shikakai accounts for 0.5 to 10 wt %, or 18 to 35 wt % of the hair dye formulation.

8. A herb-based hair dye formulation selected from one of the following formulations:
a first formulation for a black color tone consisting of 14.2-16.5 Henna, 78.75-81.5 Indigo, 1.8-2.5 Manjistha, 0.95-1.5 Amla, 0.45-0.75 Bhringraj, expressed as a percentage by weight;
a second formulation for a brown color tone consisting of 31-34.5 Henna, 63-65.5 Indigo, 0.45-0.75 Manjistha, 0.45-0.75 *Hibiscus*, 0.45-0.75 Amla, 0.45-0.75 Bhringraj, 0.45-0.75 Methi, expressed as a percentage by weight;
a third formulation for a brown color tone consisting of 44-47.5 Henna, 47.75-52 Indigo, 0.95-1.25 Manjistha, 0.95-1.25 *Hibiscus*, 0.45-0.75 Amla, 0.45-0.75 Bhringraj, 0.45-0.75 Methi, expressed as a percentage by weight;
a fourth formulation for a brown color tone consisting of 37-42 Henna, 47.5-52.5 Indigo, 4.7-6.25 Manjistha, 2.3-3.25 *Hibiscus*, 0.45-0.75 Amla, 0.45-0.75 Bhringraj, 2.3-3.25 Methi, expressed as a percentage by weight;
a fifth formulation for a red color tone consisting of 38-43 Henna, 55-60 Manjistha, 0.45-0.625 *Hibiscus*, 0.45-0.625 Amla, 0.45-0.625 Bhringraj, 0.45-0.625 Methi, expressed as a percentage by weight;
a sixth formulation for a red color tone consisting of 44.5-50 Henna, 34.5-40 Indigo, 9.5-12.25 Manjistha, 4.7-6.5 *Hibiscus*, 0.45-0.625 Amla, 0.45-0.625 Bhringraj, expressed as a percentage by weight;
a seventh formulation for a red brown color tone consisting of 55-60 Henna, 38-43 Indigo, 0.45-0.625 *Hibiscus*, 0.45-0.625 Amla, 0.45-0.625 Bhringraj, 0.45-0.625 Methi, expressed as a percentage by weight;
an eighth formulation for a blonde color tone consisting of 28.5-32 Henna, 26.5-30 Indigo, 0.45-0.625 Manjistha, 0.45-0.625 *Hibiscus*, 0.45-0.625 Amla, 0.45-0.625 Bhringraj, 38-42 *Cassia*, expressed as a percentage by weight;
a ninth formulation for a blonde color tone consisting of 28.5-32 Henna, 0.95-1.25 *Hibiscus*, 1.9-2.25 Amla, 0.95-1.25 Bhringraj, 0.95-1.25 Methi, 63-66.5 *Cassia*, expressed as a percentage by weight;
a tenth formulation for a red color tone consisting of 84-87 Henna, 9-12 Indigo, 0.95-1.25 *Hibiscus*, 1.9-2.25 Amla, 0.95-1.25 Bhringraj, expressed as a percentage by weight;
an eleventh formulation for a brown color tone consisting of 28-32 Henna, 35-38 Indigo, 0.45-0.625 Manjistha, 0.45-0.625 *Hibiscus*, 0.95-1.25 Amla, 0.45-0.625 Bhringraj, 28.5-32 *Cassia*, expressed as a percentage by weight;
a twelfth formulation for a blonde-brown color tone consisting of 0.45-0.625 Indigo, 23-27 Amla, 0.45-0.625 Bhrami, 0.45-0.625 Bhringraj, 71.25-75.5 *Cassia*, expressed as a percentage by weight;
a thirteenth formulation for a blonde color tone consisting of 23.5-28.5 Indigo, 70-75 Amla, 0.45-0.625 Bhrami, 0.45-0.625 Bhringraj, 0.45-0.625 *Cassia*, expressed as a percentage by weight;
a fourteenth formulation for a blonde-brown color tone consisting of 23.5-27 Indigo, 23.5-27 Amla, 23.5-27 Bhrami, 23.5-27 Bhringraj, expressed as a percentage by weight;
a fifteenth formulation for a blonde color tone consisting of 23.5-27 Henna, 23.5-27 Indigo, 28.5-32 *Hibiscus*, 9.5-11.5 Amla, 9.5-11.5 Methi, expressed as a percentage by weight;
a sixteenth formulation for a violet color tone consisting of 76-82 Indigo, 4-6.25 Manjistha, 4-6.25 *Hibiscus*, 9.5-12.5 Methi, expressed as a percentage by weight;
a seventeenth formulation for a blonde color tone consisting of 7-10.25 Indigo, 0.45-0.625 Amla, 0.45-0.625 Bhrami, 0.45-0.625 Bhringraj, 88-92 *Cassia*, expressed as a percentage by weight;
an eighteenth formulation for a blonde color tone consisting of 7-10.25 Henna, 0.45-0.625 Amla, 0.45-0.625 Bhrami, 0.45-0.625 Bhringraj, 88-92 *Cassia*, expressed as a percentage by weight;
a nineteenth formulation for a red color tone consisting of color tone consisting of 18-22 Henna, 8-10 Indigo, 0.45-0.625 Amla, 0.45-0.625 Bhrami, 0.45-0.625 Bhringraj, 68-72 *Cassia*, expressed as a percentage by weight;
a twentieth formulation for a blonde color tone consisting of 4-6.25 Henna, 6.5-8.5 Indigo, 0.45-0.625 Amla, 0.45-0.625 Bhrami, 0.45-0.625 Bhringraj, 84-88 *Cassia*, expressed as a percentage by weight;
a twenty first formulation for a red color tone consisting of 6.5-8.5 Henna, 4-6.25 Indigo, 0.45-0.625 Amla, 0.45-0.625 Bhrami, 0.45-0.625 Bhringraj, 84-88 *Cassia*, expressed as a percentage by weight;
a twenty second formulation for a blonde color tone consisting of 2.5-3.5 Henna, 0.45-0.625 Amla, 0.45-0.625 Bhrami, 0.45-0.625 Bhringraj, 0.45-0.625 Methi, 94-95.5 *Cassia*, expressed as a percentage by weight;
a twenty third formulation for a blonde color tone consisting of 1.75-2.25 Henna, 0.9-1.25 Manjistha, 0.45-0.625 *Hibiscus*, 0.45-0.625 Amla, 0.45-0.625 Bhrami, 0.45-0.625 Bhringraj, 94-95.5 *Cassia*, expressed as a percentage by weight;
a twenty fourth formulation for a black color tone consisting of 8.8-11 Henna, 82-85 Indigo, 1.75-2.25 Manjistha, 1.75-2.25 Indigo extract, 0.9-1.25 Amla, 0.9-1.25 Bhrami, 0.9-1.25 Bhringraj, expressed as a percentage by weight;

a twenty fifth formulation for a brown color tone consisting of 17-20 Henna, 71-75 Indigo, 5-6.5 Manjistha, 3-5 Indigo extract, expressed as a percentage by weight;

a twenty sixth formulation for a brown color tone consisting of 35-39 Henna, 52-57 Indigo, 5-6.5 Manjistha, 2-3 Indigo extract, expressed as a percentage by weight;

a twenty seventh formulation for a no color tone consisting of 32-35 Amla, 31-35 Reetha, 31-35 Shikakai, expressed as a percentage by weight;

a twenty eighth formulation for a brown color tone consisting of 97.5-98.2 Henna, 0.45-0.625 Amla, 0.45-0.625 Bhringraj, 0.45-0.625 Reetha, 0.45-0.625 Shikakai, expressed as a percentage by weight;

a twenty ninth formulation for a brown color tone consisting of 82-87 Henna, 9-12 Indigo, 4-6.25 Cassia, expressed as a percentage by weight;

a thirtieth formulation for a brown color tone consisting of 28.5-32 Henna, 26.5-30 Indigo, 39.5-44 Cassia, expressed as a percentage by weight;

a thirty first formulation for a brown color tone consisting of 35-39 Henna, 58-62 Indigo, 2.8-4 Cassia, expressed as a percentage by weight;

a thirty second formulation for a brown color tone consisting of 13-16 Henna, 83-86 Indigo, 0.9-1.25 Cassia, expressed as a percentage by weight;

a thirty third formulation for a no color tone consisting of 28.5-33 Amla, 28.5-33 Cassia, 19-22 Reetha, 19-22 Shikakai, expressed as a percentage by weight;

a thirty fourth formulation for a brown color tone consisting of 38-43 Henna, 57-62 Indigo, expressed as a percentage by weight;

a thirty fifth formulation for a blonde color tone consisting of 35.5-37.5 Turmeric, 0.45-0.625 Amla, 0.45-0.625 Bhrami, 0.45-0.625 Bhringraj, 57.5-62 Cassia, 0.45-0.625 Reetha, 0.45-0.625 Shikakai, expressed as a percentage by weight.

9. The herb-based hair dye formulation according to claim 1, wherein agents (1) to (4) add up to 100 wt %.

10. The herb-based hair dye formulation according to claim 1, further comprising one or more further agents selected from the group consisting of a wetting agent, a hair conditioner, and an agent that imparts treatment effects to hair.

11. The herb-based hair dye formulation according to claim 1, wherein the formulation is presented in powdered form as a mixture of the agents.

12. A method for producing herb-based product, comprising the following steps of:
(1) providing fresh plant parts of desirable herbs;
(2) freeze drying of the fresh plant parts under a condition that allows for freezing of water and removal of the water from the plant parts;
(3) steam sterilization of the freeze-dried plant parts for a given duration of time to sterilize the plant parts so as to obtain the herbal ingredients; and
(4) mixing of different herbal ingredients in a desirable ratio.

13. The method according to claim 12, wherein the step of freezing drying is carried out under the combined effect of a temperature ranging from −70° C. to −40° C. and vacuum pressure to remove the water by sublimation.

14. The method according to claim 12, wherein the step of steam sterilization is carried out at a temperature ranging from 110° C. to 140° C.

15. The method according to claim 12, further comprising a step of grinding the freeze-dried plant parts into powder, and an optional step of sieving the plant part powders in order to remove any foreign body or impurities.

16. The method according to claim 12, further comprising a step of storing the freeze-dried plant parts in vacuum packing before the steps of grinding, sterilization or mixing.

17. The method according to claim 12, further comprising a step of packing the mixed herbal ingredients.

18. A method for manufacturing a herb-based hair dye formulation, the method comprising the following steps of:
(1) providing fresh plant parts of desirable herbs which are being used to formulate a hair dye formulation;
(2) freeze drying of the fresh plant parts under a condition that allows for freezing of water and removal of the water from the plant parts;
(3) steam sterilization of the freeze-dried plant parts for a given duration of time to sterilize the plant parts so as to obtain the herbal ingredients;
(4) mixing of different herbal ingredients in a ratio adapted for the hair dye formulation; and optionally
(5) packing of the mixed hair dye.

19. The method according to claim 18, wherein the step of freezing drying is carried out under the combined effect of a temperature ranging from −70° C. to −40° C. and vacuum pressure to remove the water by sublimation.

20. The method according to claim 18, wherein the step of steam sterilization is carried out at a temperature ranging from 110° C. to 140° C.

21. The method according to claim 18, wherein the herb-based hair dye formulation is as defined in claim 1.

22. The method according to claim 18, comprising the following steps in the following sequence:
(1) providing fresh plant parts of desirable herbs which are being used to formulate a hair dye formulation;
(2) freeze drying of the fresh plant parts to remove water from the plant parts by method of sublimation; 100% active and passive agents as present in herbs when it is live on plant are protected and saved during the step of freeze drying;
(3) storing the freeze-dried herb parts in vacuum pack;
(4) microfine grinding of freeze-dried herbs parts to convert into a smooth powder;
(5) mixing of different herbal powders in required ratios as per formulation in order to make different colors;
(6) steam sterilization of premixed powder; and
(7) packing of powders in desired quantity and required packs.

* * * * *